(12) United States Patent
Wu et al.

(10) Patent No.: US 11,309,299 B2
(45) Date of Patent: Apr. 19, 2022

(54) IMAGE SENSOR PACKAGE AND ENDOSCOPE

(71) Applicant: Medimaging Integrated Solution, Inc., Hsinchu (TW)

(72) Inventors: Shangyi Wu, Hsinchu (TW); Mingche Hsieh, Hsinchu (TW)

(73) Assignee: MEDIMAGING INTEGRATED SOLUTION, INC., Hsinchu (TW)

(*) Notice: Subject to any disclaimer, the term of this patent is extended or adjusted under 35 U.S.C. 154(b) by 0 days.

(21) Appl. No.: 17/097,714

(22) Filed: Nov. 13, 2020

(65) Prior Publication Data
US 2021/0249393 A1   Aug. 12, 2021

(30) Foreign Application Priority Data

Feb. 11, 2020 (TW) .................. 109104251

(51) Int. Cl.
| | |
|---|---|
| H01L 25/16 | (2006.01) |
| H05K 1/14 | (2006.01) |
| H04N 5/225 | (2006.01) |
| A61B 1/00 | (2006.01) |
| A61B 1/06 | (2006.01) |
| H05K 1/11 | (2006.01) |

(52) U.S. Cl.
CPC ........ *H01L 25/167* (2013.01); *A61B 1/00124* (2013.01); *A61B 1/00195* (2013.01); *A61B 1/0684* (2013.01); *H01L 25/165* (2013.01); *H04N 5/2253* (2013.01); *H04N 5/2256* (2013.01); *H05K 1/14* (2013.01); *H04N 2005/2255* (2013.01); *H05K 1/117* (2013.01); *H05K 2201/10287* (2013.01)

(58) Field of Classification Search
CPC ....... H01L 25/167; H01L 25/165; H05K 1/14; H05K 1/117; H05K 2201/10287; H04N 5/2253; H04N 5/2256; H04N 2005/2255; A61B 1/00195; A61B 1/0684; A61B 1/00124

See application file for complete search history.

(56) References Cited

U.S. PATENT DOCUMENTS

| | | | |
|---|---|---|---|
| 8,317,104 B2* | 11/2012 | Havens | G06K 7/10712 235/454 |
| 9,748,293 B1* | 8/2017 | Li | H01L 27/14683 |
| 10,561,306 B2* | 2/2020 | Ohno | A61B 1/00124 |

(Continued)

*Primary Examiner* — Richard A Hansell, Jr.
(74) *Attorney, Agent, or Firm* — Muncy, Geissler, Olds & Lowe, P.C.

(57) ABSTRACT

An image sensor package includes a substrate, an image sensor, a light-emitting element, and a package body. The substrate includes a plurality of first conductive contacts and a plurality of second conductive contacts. The image sensor is disposed on the substrate and electrically connected to the corresponding first conductive contacts. The light-emitting element is close to the image sensor, disposed on the substrate and electrically connected to the corresponding first conductive contacts. The package body is filled between the image sensor and the light emitting element. The above-mentioned image sensor package can achieve miniaturization, provide uniform illumination, and increase light utilization efficiency. An endoscope including the above-mentioned image sensor package is also disclosed.

28 Claims, 9 Drawing Sheets

(56) References Cited

U.S. PATENT DOCUMENTS

| | | | |
|---|---|---|---|
| 2008/0255416 A1* | 10/2008 | Gilboa | A61B 1/04 600/110 |
| 2010/0200898 A1* | 8/2010 | Lin | H01L 27/14632 257/E31.11 |
| 2016/0163681 A1* | 6/2016 | Lee | H01L 25/165 257/432 |
| 2018/0042460 A1* | 2/2018 | Wake | A61B 1/00094 |

* cited by examiner

IMAGE SENSOR PACKAGE AND ENDOSCOPE

BACKGROUND OF THE INVENTION

1. Field of the Invention

The present invention relates to an image sensor package and an endoscope, particularly to an image sensor package having an illumination element and an endoscope using the same.

2. Description of the Prior Art

Endoscopes can reach the cavities of an object, which the naked eyes are unable to see, and capture images therefrom. Therefore, endoscopes have been extensively used in medicine and industry. The application of endoscopes particularly has significant influence in medicine. Endoscopes are required to access target cavities of human bodies through various small channels. For example, a bronchoscope accesses the lung through a bronchial; a cystoscope accesses the bladder through the urethra. Hence, how to miniaturize endoscopes is an important topic in the concerned fields.

Refer to FIG. 1 for a conventional endoscope. In the conventional endoscope 10, an image-sensing element 11 and light-emitting elements 12 are disposed in a flexible circuit board 13; wires 14 are soldered to corresponding conductive contacts 131 on the flexible circuit board 13. The flexible circuit board 13 is bent to the required shape. Then, the abovementioned elements are encapsulated and fixed with a plastic material to obtain the target form in a mold-injection process. The abovementioned process is complicated, and the endoscope 10 made thereby is larger. Besides, the light-emitting elements 12 are unable to project light upward and unlikely to be disposed around the image-sensing element 11. Thus, the light utilization efficiency is lower, and the illumination is less uniform and likely to have blind spots.

Accordingly, providing a miniaturized endoscope with uniform illumination is a target the manufacturers are eager to achieve at present.

SUMMARY OF THE INVENTION

The present invention provides an image sensor package and an endoscope using the same, wherein an image sensor and at least one light-emitting element are disposed on an identical substrate and then packaged; the substrates are separated by a singulation process, whereby the size of the image sensor package and the endoscope is effectively reduced. Besides, a light entrance surface of the image sensor and a light-emitting surface of the light-emitting element are oriented toward an identical direction. Therefore, the present invention can provide uniform illumination and increase light utilization efficiency.

In one embodiment, the image sensor package comprises a substrate, an image sensor, a light-emitting element, a package body, and adapter. The substrate has a plurality of first conductive contacts and a plurality of second conductive contacts electrically connected with the plurality of corresponding first conductive contacts and the plurality of first conductive contacts and the plurality of second conductive contacts are respectively disposed on opposite surfaces of the substrate. The image sensor is disposed on the substrate and electrically connected with the plurality of corresponding first conductive contacts. The light-emitting element is disposed on the substrate, neighboring the image sensor and electrically connected with the plurality of corresponding first conductive contacts. The package body is filled between the image sensor and the light-emitting element. The adapter includes a plurality of third conductive contacts and a plurality of fourth conductive contacts electrically connected with the plurality of corresponding third conductive contacts, wherein the adapter is connected with the substrate; the plurality of third conductive contacts is electrically connected with the plurality of corresponding second conductive contacts; and a plane where the plurality of fourth conductive contacts are disposed is vertical to a surface of the substrate. The image sensor package further comprises an electric-conduction connector including a plurality of fifth conductive contacts and a plurality of sixth conductive contacts electrically connected with the plurality of corresponding fifth conductive contacts, wherein the plurality of fifth conductive contacts faces the plurality of fourth conductive contacts, and the adaptor is connected with the electric-conduction connector to facilitate electric connection of the plurality of fourth conductive contacts and the plurality of corresponding fifth conductive contacts, or the image sensor package further comprises a plurality of wires electrically connected with the fourth conductive contacts of the adapter and a protective resin body, which encapsulates the plurality of fourth conductive contacts of the adapter and connection terminals of the plurality of wires.

In one embodiment, the endoscope of the present invention comprises a pipe structure, an image sensor package, a plurality of wires, and an electric connector. The pipe structure has a first opening and a second opening. The end of the first opening is to be extended into a cavity. The image sensor package is disposed at the end of the first opening, capturing an image of the cavity and generating a corresponding electronic signal. The image sensor package comprises a substrate, an image sensor, a light-emitting element, a package body, and an adapter. The substrate has a plurality of first conductive contacts and a plurality of second conductive contacts electrically connected with the plurality of corresponding first conductive contacts and the plurality of first conductive contacts and the plurality of second conductive contacts are respectively disposed on opposite surfaces of the substrate. The image sensor is disposed on the substrate and electrically connected with the plurality of corresponding first conductive contacts. The light-emitting element is disposed on the substrate, neighboring the image sensor and electrically connected with the plurality of corresponding first conductive contacts. The package body is filled between the image sensor and the light-emitting element. The adapter includes a plurality of third conductive contacts and a plurality of fourth conductive contacts electrically connected with the plurality of corresponding third conductive contacts, wherein the adapter is connected with the substrate; the plurality of third conductive contacts is electrically connected with the plurality of corresponding second conductive contacts; and a plane where the plurality of fourth conductive contacts are disposed is vertical to a surface of the substrate. The plurality of wires is electrically connected with the plurality of corresponding fourth conductive contacts of the adapter, wherein the plurality of wires directly connected with the plurality of fourth conductive contacts of the adapter and the image sensor package further comprises a protective resin body, which encapsulates the plurality of fourth conductive contacts of the adapter and connection terminals of the plurality of wires; or the image sensor package further comprises an electric-conduction connector including a plurality of fifth conductive contacts and a plurality of sixth conductive contacts electrically connected with the plurality of corresponding fifth conductive contacts, wherein the plurality of fifth conductive contacts faces the plurality of fourth conductive contacts, the adaptor is connected with the electric-conduction connector to facilitate electric connection of the plurality of fourth conductive contacts and the plurality of corresponding fifth conductive contacts, and the plurality of wires electrically connected with the plurality of corresponding sixth conductive contacts of the electric-conduction connector. The electric connector is electrically connected with the plurality of wires, facilitating the endoscope to electrically connect with an external electronic device in a pluggable manner.

The objective, technologies, features and advantages of the present invention will become apparent from the following description in conjunction with the accompanying drawings wherein certain embodiments of the present invention are set forth by way of illustration and example.

BRIEF DESCRIPTION OF THE DRAWINGS

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

Various embodiments of the present invention will be described in detail below and illustrated in conjunction with the accompanying drawings. In addition to these detailed descriptions, the present invention can be widely implemented in other embodiments, and apparent alternations, modifications and equivalent changes of any mentioned embodiments are all included within the scope of the present invention and based on the scope of the Claims. In the descriptions of the specification, in order to make readers have a more complete understanding about the present invention, many specific details are provided; however, the present invention may be implemented without parts of or all the specific details. In addition, the well-known steps or elements are not described in detail, in order to avoid unnecessary limitations to the present invention. Same or similar elements in Figures will be indicated by same or similar reference numbers. It is noted that the Figures are schematic and may not represent the actual size or number of the elements. For clearness of the Figures, some details may not be fully depicted.

Figure 2:
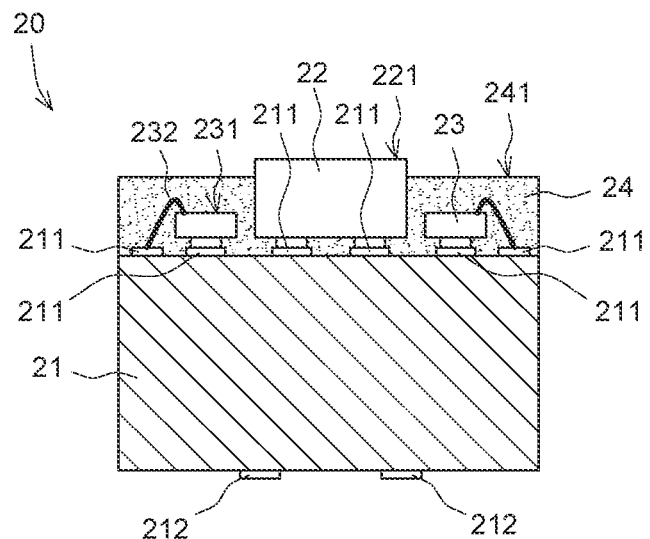
FIG. 2 is a diagram schematically showing an image sensor package according to a first embodiment of the present invention.

Refer to FIG. 2. In one embodiment of the present invention, the image sensor package 20 comprises a substrate 21, an image sensor 22, a light-emitting element 23, and a package body 24. The substrate 21 has a plurality of first conductive contacts 211 and a plurality of second conductive contacts 212. The plurality of second conductive contacts 212 may be electrically connected with the plurality of corresponding first conductive contacts 211 through interconnection structures. In one embodiment, the plurality of first conductive contacts 211 and the plurality of second conductive contacts 212 are respectively disposed on the opposite surfaces of the substrate 21, whereby the size of the substrate 21 can be reduced. In one embodiment, the substrate 21 may be made of a ceramic material or an appropriate material.

The image sensor 22 is disposed on the substrate 21 and electrically connected with the plurality of corresponding first conductive contacts 211.

The image sensor 22 may be a CMOS-based image sensor or another appropriate image sensor, wherein CMOS is the abbreviation of "Complementary Metal Oxide Semiconductor". In one embodiment, the image sensor 22 may be integrated with an imaging lens, whereby the size of the image sensor 22 can be reduced.

The light-emitting element 23 is disposed on the substrate 21 and neighbors the image sensor 22. In one embodiment, the light-emitting element 23 may be electrically connected with the first conductive contacts 211 by wires 232 in a wire-bonding process. Alternatively, the light-emitting element 23 may be electrically connected with the first conductive contacts 211 in a Flip-Chip technology or a Tape Automatic Bonding (TAB) technology.

The package body 24 is filled between the image sensor 22 and the light-emitting element 23. In the embodiment shown in FIG. 2, the package body 24 covers the light-emitting element 23. In one embodiment, the height of a light entrance surface 221 of the image sensor 22 is equal to or larger than the height of a top surface 241 of the package body 24 lest the package body 24 cover the light entrance surface 221 of the image sensor 22 and affect the image quality.

Figure 3:
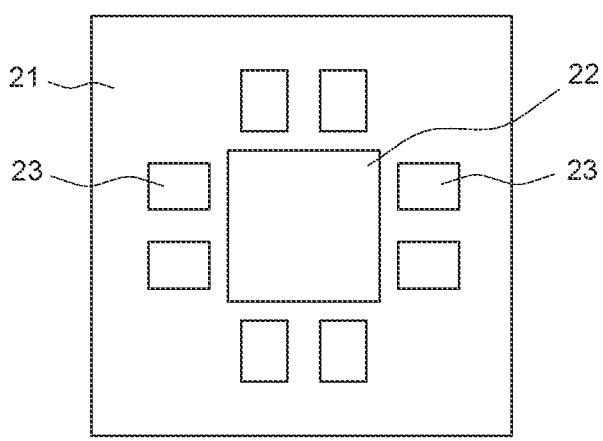
FIG. 3 is a top view schematically showing an image sensor package according to one embodiment of the present invention.

Refer to FIG. 2 and FIG. 3. In one embodiment, the image sensor package 20 comprises a plurality of light-emitting elements 23, and the plurality of light-emitting elements 23 is disposed around the image sensor 22. It is easily understood: the light-emitting elements 23 that respectively generate illumination lights with different ranges of wavelengths may be selectively adopted according to the requirement of observation. For example, the light-emitting elements 23 may be white LED (Light-emitting Diode), infrared LED, blue LED, ultraviolet LED, or a combination thereof. In one embodiment, the light-emitting element 23 may be a naked chip of LED. In one embodiment, the light-emitting element 23 includes a secondary optical structure for adjusting the light output angle.

Figure 1:
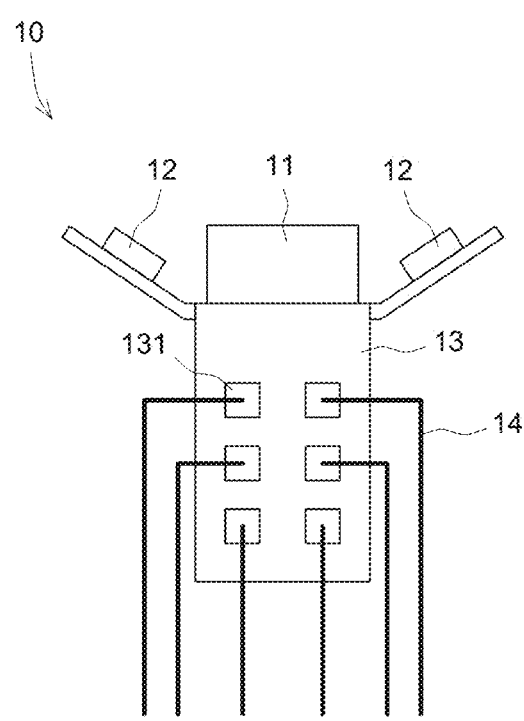
FIG. 1 is a diagram schematically showing a conventional endoscope.

According to the foregoing structure, a plurality of the substrates 21 may be connected with each other in a substrate array before package is completed. For example, a plurality of substrate units are formed on a single carrier plate, and then the image sensors 22 and the light-emitting elements 23 are arranged on the substrate units. After the image sensors 22 and the light-emitting elements 23 are packaged with the package body 24, the carrier plate is cut in a singulation process to separate the substrate units and form the structure of the substrates 21 shown in FIG. 2. Compared with the structure shown in FIG. 1 that is packaged individually, the image sensor package 20 of the present invention has a smaller size. For example, the image sensor 22 with 400×400 pixels may have a size smaller than 2 mm×2 mm, or even smaller than 1.8 mm×1.8 mm, in the present invention.

It is easily understood: the relative altitude of the image sensor 22 and the light-emitting element 23 may influence illumination and image quality. For example, if the height of the light-emitting surface 231 of the light-emitting element 23 is less than the height of the image sensor 22, the image sensor 22 may block the illumination light emitted by the light-emitting element 23, which may result in shadows. If the height of the light-emitting surface 231 of the light-emitting element 23 is more than the height of the light entrance surface 221 of the image sensor 22, the light-emitting element 23 may block the light reflected from the observed object or the light emitted from the light-emitting element 23 may irradiate directly on the image sensor 22, which may degrade image quality. Refer to the embodiment shown in FIG. 2, in order to optimize illumination and image quality, the height of the light entrance surface 221 of the image sensor 22 is equal to or larger than the height of the light-emitting surface 231 of the light-emitting element 23. In one embodiment, the difference between the height of the light entrance surface 221 of the image sensor 22 and the height of the light-emitting surface 231 of the light-emitting element 23 is equal to or less than 1 mm. It is preferred: the difference between the height of the light entrance surface 221 of the image sensor 22 and the height of the light-emitting surface 231 of the light-emitting element 23 is equal to or less than 0.5 mm. It can be understood that the light entrance surface refers to the outermost surface of the image sensor module. For example, when the image sensor module includes at least one lens, the light entrance surface refers to the outermost surface of the lens.

Figure 4:
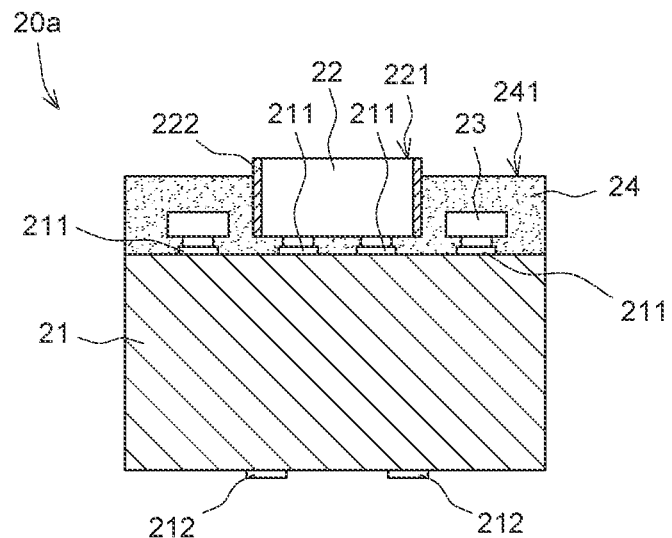
FIG. 4 is a diagram schematically showing an image sensor package according to a second embodiment of the present invention.

The illumination light emitted by the light-emitting element 23 may directly enter the imaging system of the image sensor 22. For example, the illumination light emitted by the light-emitting element 23 may enter the region between the image sensor 23 and the imaging lens, which may result in image whitening and degrade image quality. Refer to FIG. 4. In one embodiment, the image sensor 22 of the image sensor package 20a comprises a light-shielding layer 222, which is disposed between the image sensor 22 and the light-emitting element 23, whereby to overcome the abovementioned problem. For example, the light-shielding layer 222 is arranged on the sidewall of the image sensor 22. The light-shielding layer 222 prevents the illumination light, which is emitted by the light-emitting element 23, from directly entering the imaging system of the image sensor 22 lest the image quality be degraded.

Figure 5:
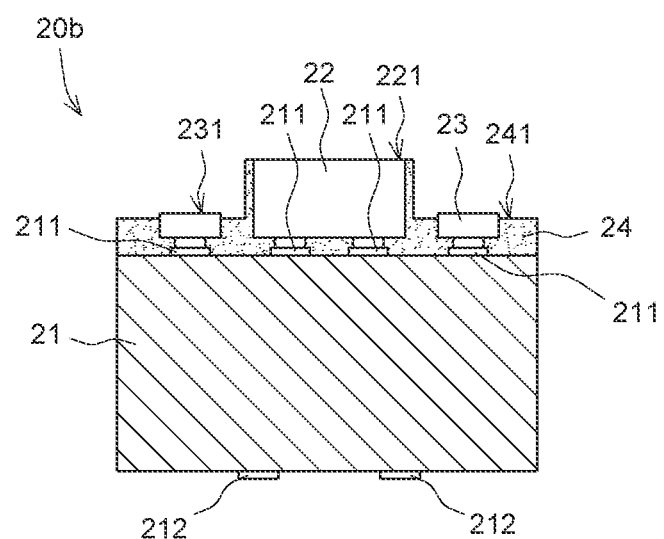
FIG. 5 is a diagram schematically showing an image sensor package according to a third embodiment of the present invention.

In one embodiment, the package body 24 is made of an opaque resin, whereby to prevent the illumination light, which is emitted by the light-emitting element 23, from directly entering the imaging system of the image sensor 22. It is easily understood: the light-emitting surface 231 of the light-emitting element 23 must be exposed from the package body 24 lest the light output of the light-emitting element 23 be affected. In other words, the package body 24 cannot cover the light-emitting surface 231 of the light-emitting element 23, as shown in the image sensor package 20b of FIG. 5.

Figure 6A:
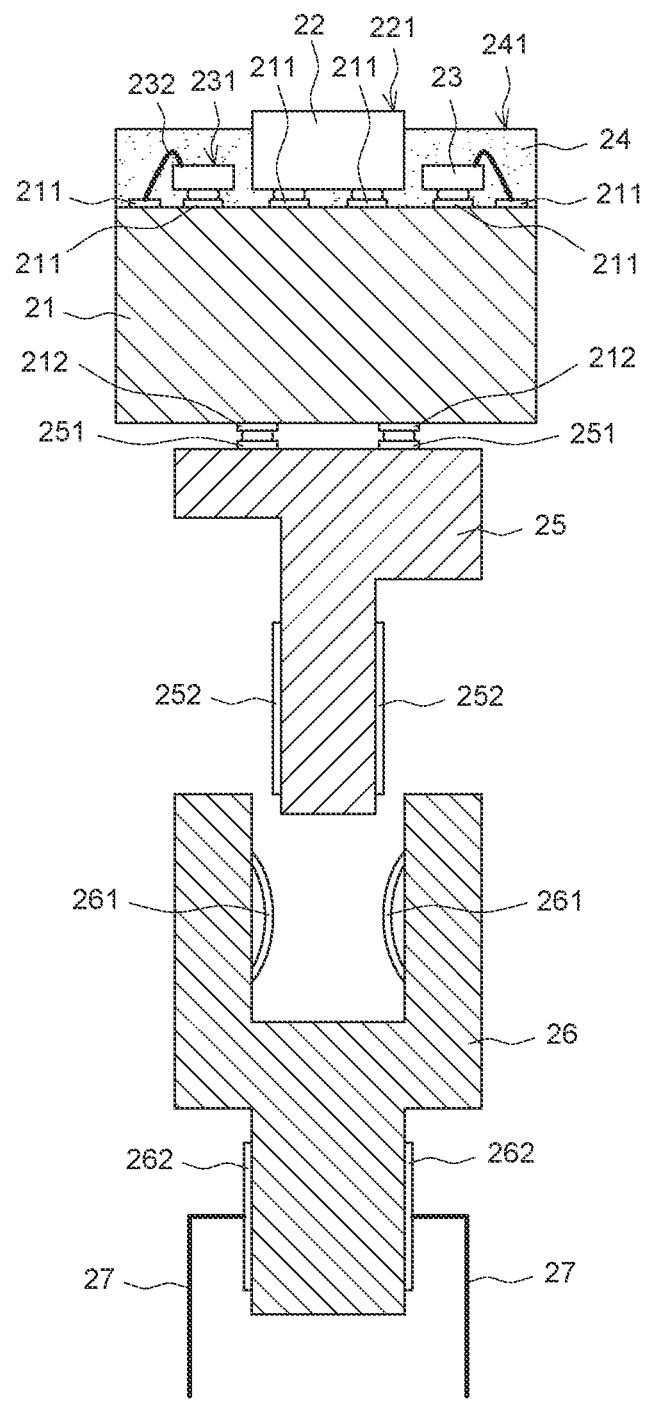
FIG. 6a is a diagram schematically showing an image sensor package according to a fourth embodiment of the present invention.

Refer to FIG. 6a. In one embodiment, the image sensor package of the present invention further comprises an adapter 25. The adapter 25 includes a plurality of third conductive contacts 251 and a plurality of fourth conductive contacts 252. The plurality of fourth conductive contacts 252 may be electrically connected with the plurality of corresponding third conductive contacts 251. In one embodiment, the adapter 25 is connected with the substrate 12 in a Surface-Mount Technology (SMT) or an Anisotropic Conductive Film (ACF) technology, whereby the plurality of third conductive contacts 251 can be electrically connected with the plurality of corresponding second conductive contacts 212. The adapter 25 may vary the way in which the substrate 21 is electrically connect with the external circuit. The plane where the second conductive contacts 212 are disposed is essentially parallel to the surface of the substrate 21. However, the plane where the fourth conductive contacts 252 are disposed may be vertical to the surface of the substrate 21 via the following design of the present invention: the fourth conductive contacts 252 are electrically connected with the second conductive contacts 212 through the third conductive contacts 251, and thus the position and direction of the fourth conductive contacts 252 may be arbitrarily adjusted. Thereby is favored the electric connection between the image sensor package and an external circuit.

Refer to FIG. 6a. In one embodiment, the image sensor package of the present invention further comprises an electric-conduction connector 26. The electric-conduction connector 26 includes a plurality of fifth conductive contacts 261 and a plurality of sixth conductive contacts 262. The plurality of sixth conductive contacts 262 may be electrically connected with the plurality of corresponding fifth conductive contacts 261 through an interconnection structure. The structure of the electric-conduction connector 26 is complementary to the structure of the adapter 25. While the adaptor 25 is connected with the electric-conduction connector 26, the plurality of fourth conductive contacts 252 of the adapter 25 is electrically connected with the plurality of corresponding fifth conductive contacts 261 of the electric-conduction connector 26.

In one embodiment, the fifth conductive contact 261 of the electric-conduction connector 26 is a metallic spring plate, whereby while the adapter 25 is inserted into the electric-conduction connector 26, the fifth conductive contact 261 of the electric-conduction connector 26 elastically presses against the fourth conductive contact 252 of the adapter 25 to form an electric connection. However, the present invention is not limited by the embodiment. In one embodiment, a conductive paste is applied onto the fourth conductive contacts 252 of the adapter 25 or the fifth conductive contacts 261 of the electric-conduction connector 26, whereby while the adapter 25 is inserted into the electric-conduction connector 26, the conductive paste forms an electric conduction between the fourth conductive contacts 252 of the adapter 25 and the fifth conductive contacts 261 of the electric-conduction connector 26, and whereby the adapter 25 is secured in the electric-conduction connector 26.

Figure 6B:
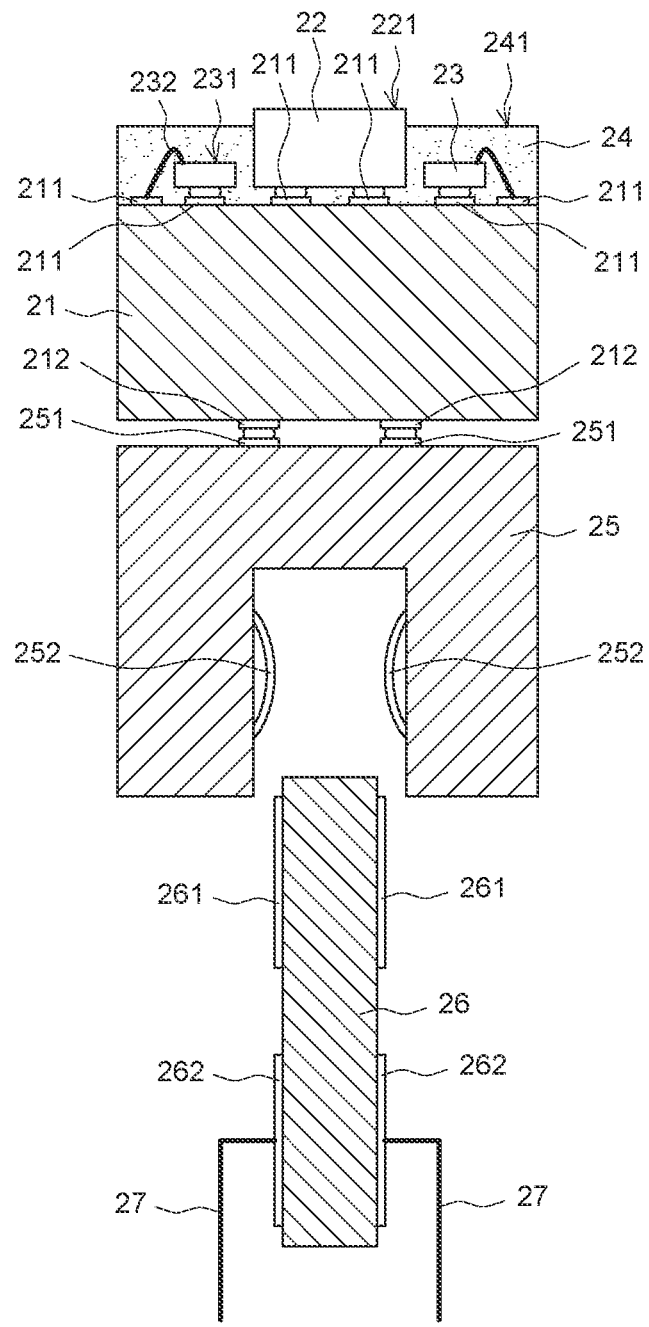
FIG. 6b is a diagram schematically showing an image sensor package according to a fifth embodiment of the present invention.

In the embodiment shown in FIG. 6a, the adapter 25 has a male connector structure, and the electric-conduction connector 26 has a female connector structure. However, the present invention is not limited by the embodiment. Refer to FIG. 6b. In one embodiment, the adapter 25 has a female connector structure, and the electric-conduction connector 26 has a male connector structure. It is easily understood: any structure that favors the press-fit engagement and electric connection between the adapter 25 and the electric-conduction connector 26 may be used by the present invention.

Based on the abovementioned structure, while wires 27 are electrically connected with the sixth conductive contacts 262 of the electric-conduction connector 26, the image sensor 22 and the light-emitting element 23 on the substrate 21 are electrically connected with the external circuit. It is easily understood: the process to electrically connect the wires 27 with the sixth conductive contacts 262 of the electric-conduction connector 26 and the process to electrically connect the adapter 25 with the substrate 21 may be separately performed. After the electric-connection processes are respectively completed, the substrate 21 containing the adapter 25 is connected with the electric-conduction connector 26 to form a complete circuit. The abovementioned processes not only shorten the time of the overall fabrication process but also prevent from the elements repeatedly experiencing high-temperature processes of soldering wires.

Figure 7:
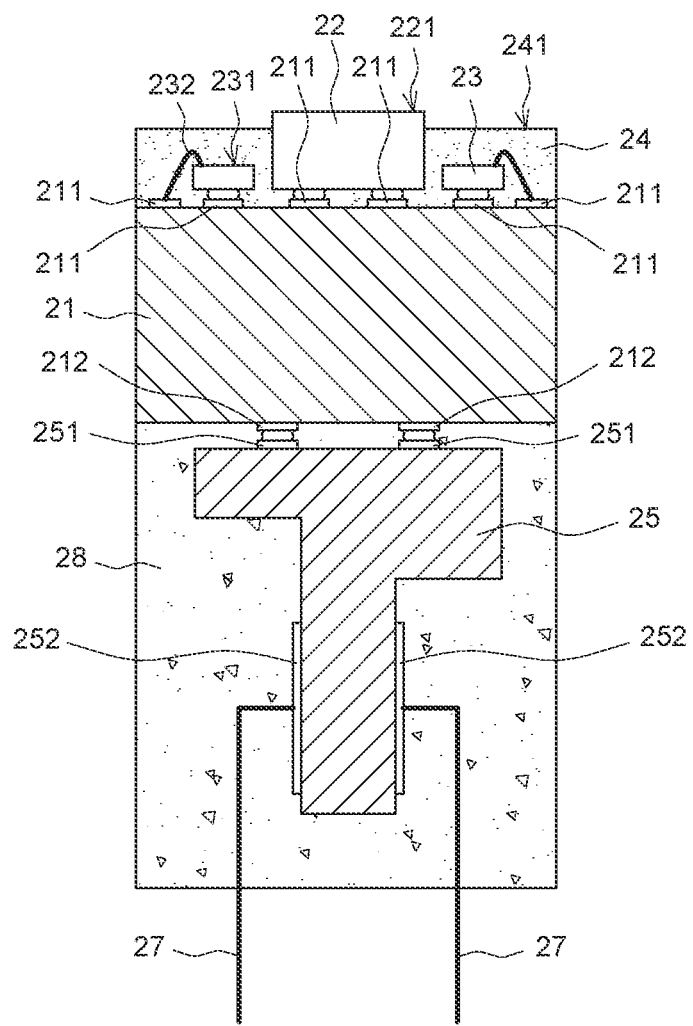
FIG. 7 is a diagram schematically showing an image sensor package according to a sixth embodiment of the present invention.

Refer to FIG. 7. In one embodiment, the electric-conduction connector 26 is omitted, and the wires 27 are directly soldered to the fourth conductive contacts 252 of the adapter 25. In one embodiment, the image sensor package of the present invention comprises a protective resin body 28. The protective resin body 28 encapsulates the plurality of fourth conductive contacts 252 of the adapter 25 and the connection terminals of the wires 27, whereby to enhance the connection strength between the wires 27 and the fourth conductive contacts 252 and increase the reliability of the system.

Figure 8:
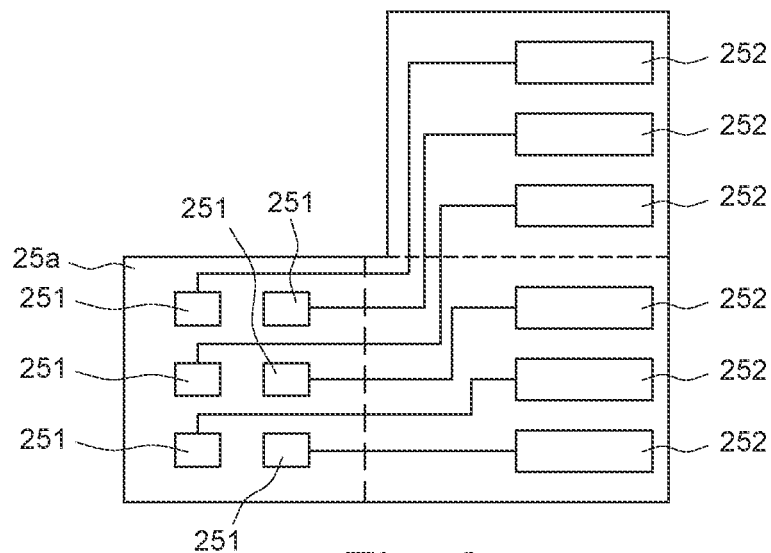
FIG. 8 is a diagram schematically showing an adapter of an image sensor package according to a seventh embodiment of the present invention.
Figure 9:
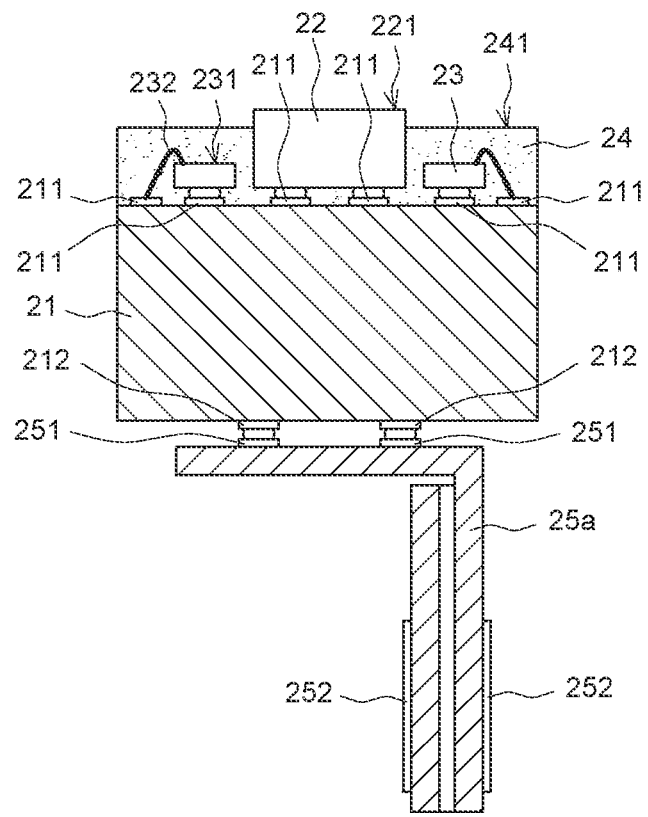
FIG. 9 is a diagram schematically showing an image sensor package according to the seventh embodiment of the present invention.

In the embodiments shown in FIG. 6a, FIG. 6b and FIG. 7, the adapters 25 are rigid ones. However, the present invention is not limited by these embodiments. In one embodiment, the adapter 25 is a flexible circuit board. Refer to FIG. 8. In a flexible adapter 25a, a plurality of third conductive contacts 251 and a plurality of fourth conductive contacts 252 are formed on a flexible circuit board. Then, the flexible circuit board is bent 90 degrees along the long-dash line in FIG. 8; next, the flexible circuit board is bent 180 degrees along the short-dash line in FIG. 8; thus is formed the adapter 25a shown in FIG. 9. As the center-folded flexible circuit board has sufficient strength, it can be directly inserted into the electric-conduction connector 26 shown in FIG. 6a. Alternatively, the wires 27 is directly soldered to the fourth conductive contacts 252 of the adapter 25a.

Figure 10:
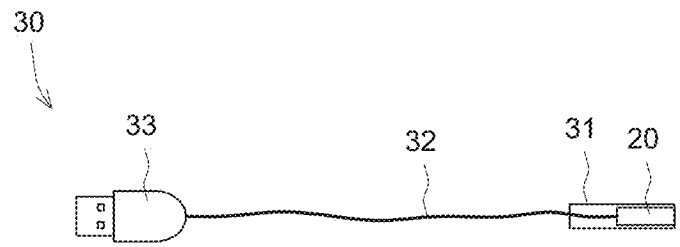
FIG. 10 is a diagram schematically showing an endoscope according to an eighth embodiment of the present invention.

Refer to FIG. 10. In one embodiment, the endoscope 30 of the present invention comprises a pipe structure 31, an image sensor package 20, a plurality of wires 32, and an electric connector 33. The pipe structure 31 has a first opening and a second opening. The end of the first opening is to be extended into a cavity, such as a cavity of a human body or a tiny space in an industrial inspection. It is easily understood: the pipe structure 31 may be designed to have different shapes according to requirement. The image sensor package 20 is disposed at the end of the first opening, capturing images of the cavity and generating corresponding electronic signals. The structure of the image sensor package 20 has been described in detail and will not repeat herein.

The wires 32 are electrically connected with the image sensor package 20 and the electric connector 33, whereby the electronic signal generated by the image sensor package 20 can be sent through the electric connector 33 to an external electronic device, such as a computer, a mobile Internet access device, or a dedicated electronic device of the endoscope. In one embodiment, the electric connector 33 may be connected with an external electronic device in a pluggable manner. For example, the electric connector 33 may be a USB interface, a connection interface of a mobile Internet access device, or another appropriate electric connector.

Figure 11:
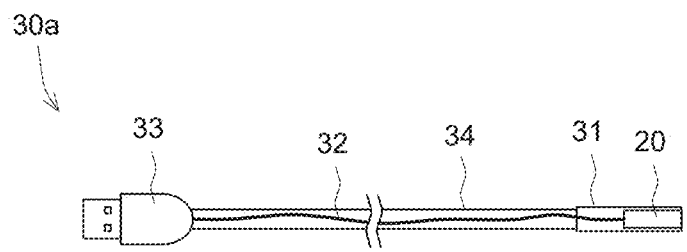
FIG. 11 is a diagram schematically showing an endoscope according to a ninth embodiment of the present invention.

Refer to FIG. 11. In one embodiment, the endoscope 30a of the present invention comprises an extension tube 34. One end of the extension tube 34 is connected with the end of the second opening of the pipe structure 31, and the other end of the extension tube 34 is connected with the electric connector 33. The extension tube 34 can protect the plurality of wires 32 disposed inside the extension tube 34 and provide appropriate strength to enable the pipe structure 31 to extend to the deep of a cavity of an object.

Figure 12:
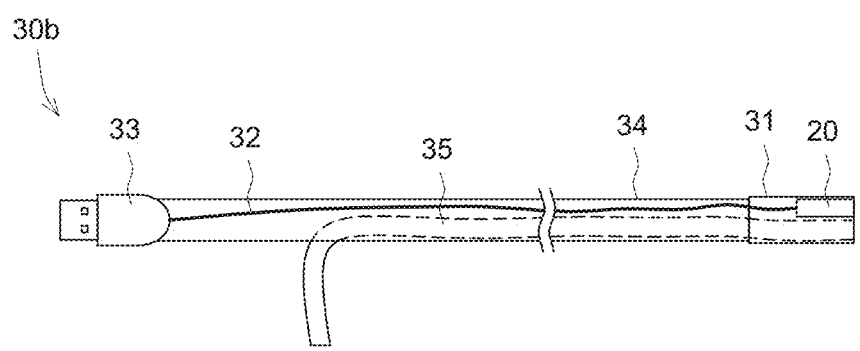
FIG. 12 is a diagram schematically showing an endoscope according to a tenth embodiment of the present invention.

Refer to FIG. 12. In one embodiment, the pipe structure 31 of the endoscope 30b of the present invention includes a working channel 35. The operator may extend a working instrument through the working channel into a cavity to undertake a desired work, such as sampling a tissue, sucking/removing secretion, tissue fluid or blood, or supplying medicine.

Figure 13:
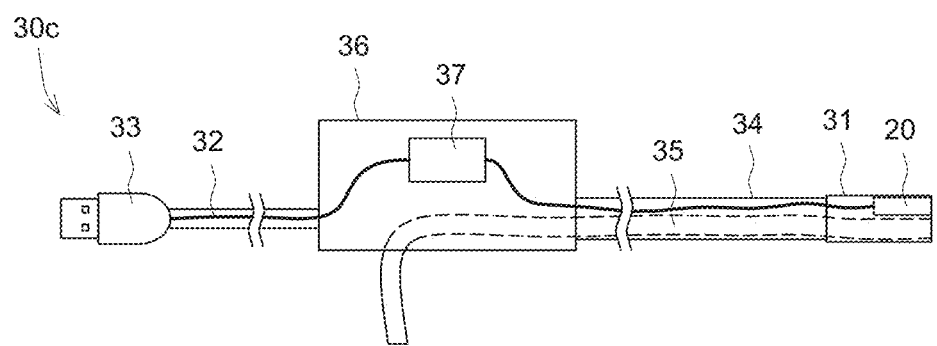
FIG. 13 is a diagram schematically showing an endoscope according to an eleventh embodiment of the present invention.

Refer to FIG. 13. In one embodiment, the endoscope 30c of the present invention comprises a casing 36, which is disposed between the pipe structure 31 and the electric connector 33. The casing 36 may be designed to have different appearances according to different requirements. For example, the casing 36 may have a shape suitable to be held by the hand of the operator. Alternatively, the casing 36 may have a shape where a carrier, such as a head-mounted carrier, can be mounted. In one embodiment, the endoscope 30c of the present invention comprises an electronic element 37, which is electrically connected with the image sensor package 20 and the electric connector 33. The electronic element 37 can process the electronic signals generated by the image sensor package 20 and send the electronic signals to an external electronic device. In one embodiment, the electronic element 37 is a micro control unit (MCU).

In conclusion, the present invention proposes an image sensor package and an endoscope using the same, wherein an image sensor and at least one light-emitting element are disposed on an identical substrate. After packaging, a plurality of substrates connected to each other is separated by a singulation process. Thereby, the size of the image sensor package and the endoscope of the present invention can be effectively reduced. Further, the light entrance surface of the image sensor and the light-emitting surfaces of the light-emitting elements are oriented to the same direction, and a plurality of light-emitting elements is disposed around the image sensor. Thereby, the image sensor package and the endoscope of the present invention can provide uniform illumination and increase the light utilization efficiency. Furthermore, the adapter can facilitate the adjustment of the position and direction of the conductive contacts, by which the substrate is connected to an external circuit. Thereby, the succeeding process can be greatly simplified. Thus, the time of the overall fabrication process is shortened, and the elements are exempted from repeatedly experiencing high-temperature processes.

While the invention is susceptible to various modifications and alternative forms, a specific example thereof has been shown in the drawings and is herein described in detail. It should be understood, however, that the invention is not to be limited to the particular form disclosed, but to the contrary, the invention is to cover all modifications, equivalents, and alternatives falling within the appended claims.

What is claimed is:

1. An image sensor package comprising:
   a substrate including a plurality of first conductive contacts and a plurality of second conductive contacts, wherein the plurality of first conductive contacts and the plurality of second conductive contacts are respectively disposed on opposite surfaces of the substrate, and the plurality of second conductive contacts is electrically connected with the plurality of corresponding first conductive contacts;
   an image sensor disposed on the substrate and electrically connected with the plurality of corresponding first conductive contacts;
   a light-emitting element disposed on the substrate, neighboring the image sensor, and electrically connected with the plurality of corresponding first conductive contacts;
   a package body filled between the image sensor and the light-emitting element; and
   an adapter including a plurality of third conductive contacts and a plurality of fourth conductive contacts electrically connected with the plurality of corresponding third conductive contacts, wherein the adapter is connected with the substrate; the plurality of third conductive contacts is electrically connected with the plurality of corresponding second conductive contacts; and a plane where the plurality of fourth conductive contacts are disposed is vertical to a surface of the substrate;
   wherein the image sensor package further comprises an electric-conduction connector including a plurality of fifth conductive contacts and a plurality of sixth conductive contacts electrically connected with the plurality of corresponding fifth conductive contacts, wherein the plurality of fifth conductive contacts faces the plurality of fourth conductive contacts, and the adaptor is connected with the electric-conduction connector to facilitate electric connection of the plurality of fourth conductive contacts and the plurality of corresponding fifth conductive contacts; or
   the image sensor package further comprises a plurality of wires electrically connected with the fourth conductive contacts of the adapter; and a protective resin body, which encapsulates the plurality of fourth conductive contacts of the adapter and connection terminals of the plurality of wires.

2. The image sensor package according to claim 1, wherein a height of a light entrance surface of the image sensor is equal to or greater than a height of a light-emitting surface of the light-emitting element.

3. The image sensor package according to claim 1, wherein a height of a light entrance surface of the image sensor is greater than a height of a light-emitting surface of the light-emitting element; a difference of the height of the light entrance surface of the image sensor and the height of the light-emitting surface of the light-emitting element is equal to or less than 1 mm.

4. The image sensor package according to claim 1, wherein a height of a light entrance surface of the image sensor is equal to or greater than a height of a top surface of the package body.

5. The image sensor package according to claim 1, wherein the package body covers the light-emitting element.

6. The image sensor package according to claim 1, wherein a light-emitting surface of the light-emitting element is exposed from the package body; the package body is made of an opaque resin.

7. The image sensor package according to claim 1, wherein the image sensor includes a light-shielding layer; the light-shielding layer is disposed between the image sensor and the light-emitting element.

8. The image sensor package according to claim 1, wherein the image sensor includes an imaging lens.

9. The image sensor package according to claim 1, wherein the adapter is a rigid adapter or a flexible circuit board.

10. The image sensor package according to claim 1, wherein the substrate is made of a ceramic material.

11. The image sensor package according to claim 1, wherein the image sensor package comprises a plurality of the light-emitting elements, and the plurality of light-emitting elements is disposed around the image sensor.

12. The image sensor package according to claim 1, wherein the light-emitting element is a white LED (Light-emitting Diode), an infrared LED, a blue LED, an ultraviolet LED, or a combination thereof.

13. An endoscope comprising:
    a pipe structure having a first opening and a second opening, wherein an end of the first opening of the pipe structure is to be extended into a cavity;
    an image sensor package disposed at the end of the first opening, capturing an image of the cavity, and generating a corresponding electronic signal, wherein the image sensor package comprises:
    a substrate including a plurality of first conductive contacts and a plurality of second conductive contacts, wherein the plurality of first conductive contacts and the plurality of second conductive contacts are respectively disposed on opposite surfaces of the substrate, and the plurality of second conductive contacts is electrically connected with the plurality of corresponding first conductive contacts;
    an image sensor disposed on the substrate and electrically connected with the plurality of corresponding first conductive contacts;
    a light-emitting element disposed on the substrate, neighboring the image sensor, and electrically connected with the corresponding first conductive contacts; and
    a package body filled between the image sensor and the light-emitting element;
    an adapter including a plurality of third conductive contacts and a plurality of fourth conductive contacts electrically connected with the plurality of corresponding third conductive contacts, wherein the adapter is connected with the substrate; the plurality of third conductive contacts is electrically connected with the plurality of corresponding second conductive contacts; and a plane where the plurality of fourth conductive contacts are disposed is vertical to a surface of the substrate;

a plurality of wires electrically connected with the plurality of corresponding fourth conductive contacts of the adapter; and an electric connector electrically connected with the plurality of wires and for electric connection with an external electronic device in a pluggable manner;

wherein the plurality of wires directly connected with the plurality of fourth conductive contacts of the adapter, and the image sensor package further comprises a protective resin body, which encapsulates the plurality of fourth conductive contacts of the adapter and connection terminals of the plurality of wires; or the image sensor package further comprises an electric-conduction connector including a plurality of fifth conductive contacts and a plurality of sixth conductive contacts electrically connected with the plurality of corresponding fifth conductive contacts, wherein the plurality of fifth conductive contacts faces the plurality of fourth conductive contacts, the adaptor is connected with the electric-conduction connector to facilitate electric connection of the plurality of fourth conductive contacts and the plurality of corresponding fifth conductive contacts, and the plurality of wires electrically connected with the plurality of corresponding sixth conductive contacts of the electric-conduction connector.

14. The endoscope according to claim 13 further comprising:
an extension tube, wherein one end of the extension tube is connected with an end of the second opening of the pipe structure, and another end of the extension tube is connected with the electric connector; the plurality of wires is disposed inside the extension tube.

15. The endoscope according to claim 13 further comprising:
an electronic element, which is electrically connected with the image sensor package and the electric connector to process electronic signals generated by the image sensor package.

16. The endoscope according to claim 13, wherein the pipe structure further includes a working channel.

17. The endoscope according to claim 13 further comprising:
a casing, which is disposed between the pipe structure and the electric connector.

18. The endoscope according to claim 13, wherein a height of a light entrance surface of the image sensor is equal to or greater than a height of a light-emitting surface of the light-emitting element.

19. The endoscope according to claim 13, wherein a height of a light entrance surface of the image sensor is greater than a height of a light-emitting surface of the light-emitting element; a difference of the height of the light entrance surface of the image sensor and the height of the light-emitting surface of the light-emitting element is equal to or less than 1 mm.

20. The endoscope according to claim 13, wherein a height of a light entrance surface of the image sensor is equal to or greater than a height of a top surface of the package body.

21. The endoscope according to claim 13, wherein the package body covers the light-emitting element.

22. The endoscope according to claim 13, wherein a light-emitting surface of the light-emitting element is exposed from the package body; the package body is made of an opaque resin.

23. The endoscope according to claim 13, wherein the image sensor includes a light-shielding layer; the light-shielding layer is disposed between the image sensor and the light-emitting element.

24. The endoscope according to claim 13, wherein the image sensor includes an imaging lens.

25. The endoscope according to claim 13, wherein the adapter is a rigid adapter or a flexible circuit board.

26. The endoscope according to claim 13, wherein the substrate is made of a ceramic material.

27. The endoscope according to claim 13, wherein the image sensor package comprises a plurality of the light-emitting elements, and the plurality of light-emitting elements is disposed around the image sensor.

28. The endoscope according to claim 13, wherein the light-emitting element is a white LED (Light-emitting Diode), an infrared LED, a blue LED, an ultraviolet LED, or a combination thereof.

* * * * *